United States Patent

Schenke et al.

Patent Number: 5,071,999
Date of Patent: Dec. 10, 1991

[54] PREPARATION OF 2,7-DIAZABICYCLO[3.3.0]OCTANES

[75] Inventors: Thomas Schenke, Bergisch-Gladbach; Uwe Petersen, Leverkusen, both of Fed. Rep. of Germany

[73] Assignee: Bayer Aktiengesellschaft, Leverkusen, Fed. Rep. of Germany

[21] Appl. No.: 507,938

[22] Filed: Apr. 10, 1990

[30] Foreign Application Priority Data

Apr. 17, 1989 [DE] Fed. Rep. of Germany ....... 3912509
Oct. 3, 1989 [DE] Fed. Rep. of Germany ....... 3932903

[51] Int. Cl.⁵ .......................................... C07D 487/02
[52] U.S. Cl. .................................................. 548/453
[58] Field of Search ................. 548/453; 514/412, 421

[56] References Cited

U.S. PATENT DOCUMENTS 4,990,517  2/1991  Petersen et al. ..................... 514/300

FOREIGN PATENT DOCUMENTS 56673  3/1989  Japan .

OTHER PUBLICATIONS

Chiba et al., Chemical Abstracts, 111-153779w, 1989.
Justus Liebigs Ann. Chemie 677, 154 (1964).

Primary Examiner—Mary C. Lee
Assistant Examiner—Peter Davis
Attorney, Agent, or Firm—Sprung, Horn, Kramer & Woods

[57] ABSTRACT

2,7-Diazabicyclo[3.3.0]octanes, suitable for 7-position substituents or antibacterially active quinolone carboxylic acids, of the formula

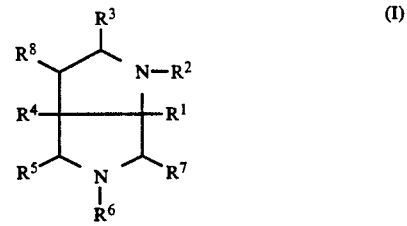

in which
$R^1$, $R^3$, $R^4$, $R^5$, $R^7$ and $R^8$ may be identical or different and in each case denote H, $C_1$–$C_5$-alkyl (optionally substituted by halogen, hydroxyl or $C_1$–$C_3$-alkoxy), $C_1$–$C_3$-alkoxycarbonyl or $C_6$–$C_{12}$-aryl,
$R^4$ additionally denotes halogen,
$R^2$ and $R^6$ may be identical or different, denote H, $C_1$–$C_6$-alkyl, benzyl, $C_6$–$C_{12}$-aryl, $C_1$–$C_3$-alkanoyl, benzoyl or $C_1$–$C_5$-alkoxycarbonyl, or
$R^2$ and $R^3$ together denote a bridge of the structure $(CH_2)_n$, $n=2$–4, $CH_2$—$CHOH$—$CH_2$, $CH_2$—$S$—$CH_2$ or $C(CH_3)_2$—$S$—$CH_2$,
excluding 2,7-diazabicyclo[3.3.0]octane.

Also their preparation by the reaction

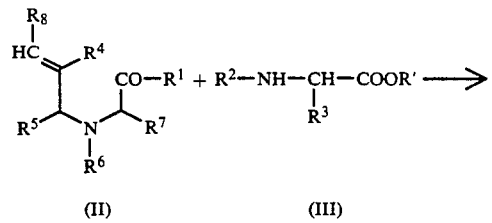

$$(I) + CO_2 + H_2O$$

Intermediates II are also new.

9 Claims, No Drawings

PREPARATION OF 2,7-DIAZABICYCLO[3.3.0]OCTANES

The present invention relates to 2,7-diazabicyclo[3.3.0]octanes and to a process for their preparation. The compounds according to the invention are useful intermediates for the preparation of highly active antibacterial quinolonecarboxylic acids.

It has already been disclosed that 2,7-diazabicyclo[3.3.0]octane (octahydropyrrolo[3,4-b]pyrrole) can be prepared by reduction with lithium aluminum hydride from 2,7-diazabicyclo[3.3.0]octane-3,8-dione. This compound was prepared by addition of diazomethane to dimethyl glutaconate and subsequent cleavage by hydrogenation of the intermediate pyrazoline derivative (Justus Liebigs Ann. Chemie 677, 154 (1964)). This process involves the disadvantage of contact with the highly toxic and explosive diazomethane and is of no use for industrial application Moreover, substituted glutaconic acid esters can only be prepared with difficulty, so that this process is not easily capable of general application.

The invention relates to 2,7-diazabicyclo[3.3.0]-octanes of the formula (I)

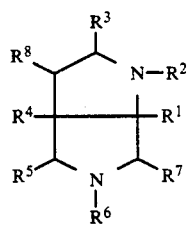

where
- $R^1$, $R^3$, $R^4$, $R^5$, $R^7$ and $R^8$ may be identical or different, in each case denote H, $C_1$-$C_5$-alkyl, optionally substituted by halogen, hydroxyl or $C_1$-$C_4$-alkoxy, $C_1$-$C_3$-alkoxycarbonyl or $C_6$-$C_{12}$-aryl, preferably H, $C_1$-$C_3$-alkyl, $C_1$-$C_3$-alkoxycarbonyl or phenyl, particularly preferably H or methyl,
- $R^4$ additionally denotes halogen, preferably fluorine, chlorine or bromine, particularly preferably chlorine or bromine,
- $R^2$ and $R^6$ may be identical or different and denote H, $C_1$-$C_6$-alkyl, benzyl, $C_6$-$C_{12}$-aryl, $C_1$-$C_3$-alkanoyl, benzoyl or $C_1$-$C_5$-alkoxycarbonyl, preferably H, $C_1$-$C_3$-alkyl, benzyl, $C_6$-$C_{12}$-aryl, $C_1$-$C_2$-alkanoyl, benzoyl or $C_1$-$C_4$-alkoxycarbonyl, particularly preferably H, methyl, phenyl, acetyl or $C_2$-$C_4$-alkoxycarbonyl and
- $R^2$ and $R^3$ together optionally denote a bridge of the structure $(CH_2)_n$, n=2-4, $CH_2$—CHOH—$CH_2$, $CH_2$—S—$CH_2$ or $C(CH_3)_2$—S—$CH_2$, excluding 2,7-diazabicyclo[3.3.0]octane.

Particularly preferred compounds are those of the following formuale:

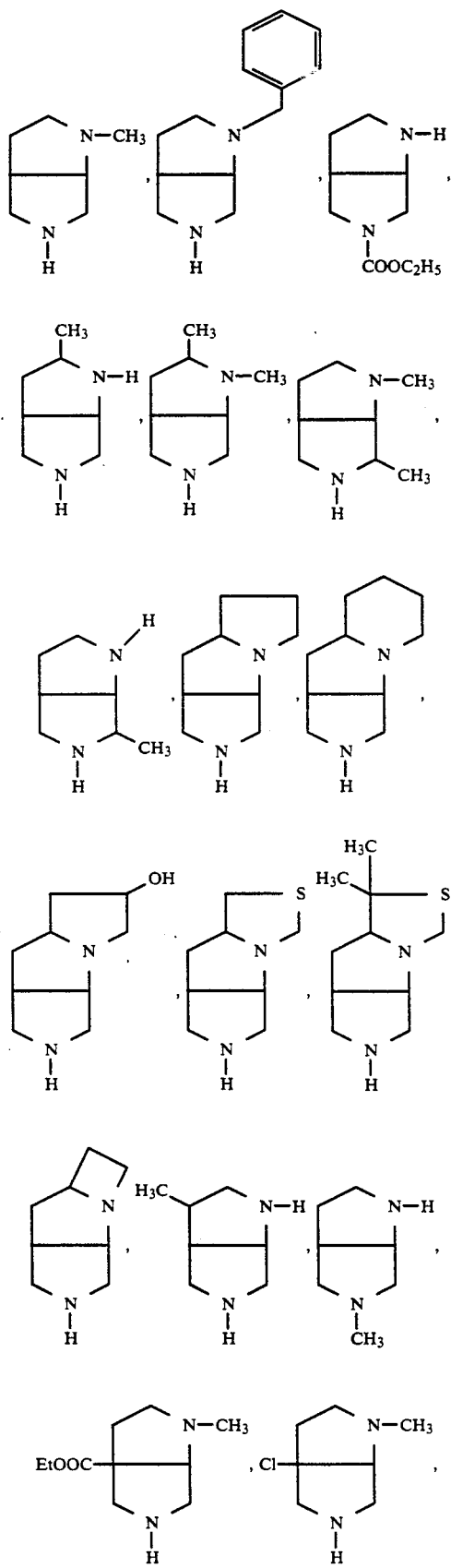

-continued

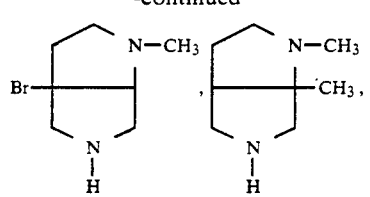

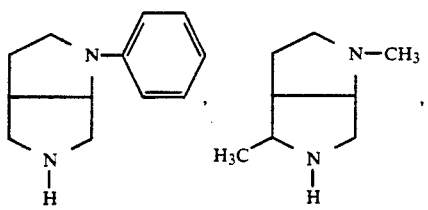

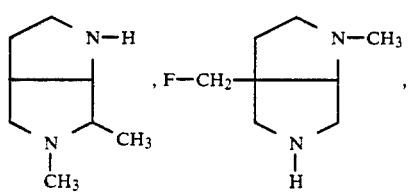

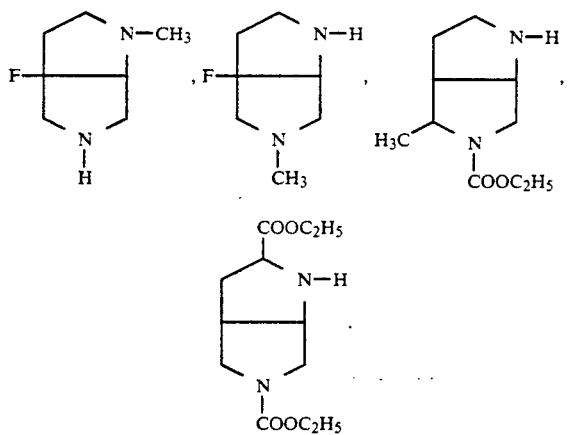

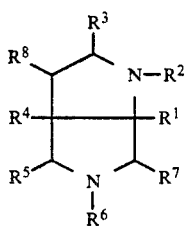

The $C_6$-$C_{12}$-aryl radical can be substituted or unsubstituted. Possible substituents are 1 to 3, preferably 1 substituent(s), from the group comprising halogen, in particular Cl, Br or F, amino, $C_1$-$C_3$-alkylamino, $C_1$-$C_3$-dialkylamino, hydroxyl, $C_1$-$C_3$-alkoxy, $C_1$-$C_3$-alkyl or cyano.

It has furthermore been found that 2,7-diazabicyclo [3.3.0]octanes of the formula (I)

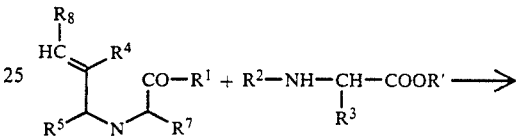

(I)

where $R^1$, $R^3$, $R^4$, $R^5$, $R^7$ and $R^8$ may be identical or different and in each case denote H, $C_1$-$C_5$-alkyl, optionally substituted by halogen, hydroxyl or $C_1$-$C_3$-alkoxy, $C_1$-$C_3$-alkoxycarbonyl or $C_6$-$C_{12}$-aryl, preferably H, $C_1$-$C_3$-alkyl, $C_1$-$C_3$-alkoxycarbonyl or phenyl, particularly preferably H and methyl, $R^4$ additionally denotes halogen, preferably fluorine, chlorine or bromine, particularly preferably chlorine or bromine, $R^2$ and $R^6$ may be identical or different and denote H, $C_1$-$C_6$-alkyl, benzyl, $C_6$-$C_{12}$-aryl, $C_1$-$C_3$-alkanoyl, benzoyl or $C_1$-$C_5$-alkoxycarbonyl, preferably H, $C_1$-$C_3$-alkyl, benzyl, $C_6$-$C_{12}$-aryl, $C_1$-$C_2$-alkanoyl, benzoyl or $C_1$-$C_4$-alkoxycarbonyl, particularly preferably H, methyl, phenyl, acetyl or $C_2$-$C_4$-alkoxycarbonyl and $R^2$ and $R^3$ together optionally denote a bridge of the structure $(CH_2)_n$, $n=2-4$, $CH_2$—$CHOH$—$CH_2$, $CH_2$—$S$—$CH_2$ or $C(CH_3)_2$—$S$—$CH_2$, are obtained by a process in which unsaturated carbonyl compounds of the formula (II) are reacted with amino acid derivatives of the formula (III) in an intramolecular 1,3-dipolar cycloaddition,

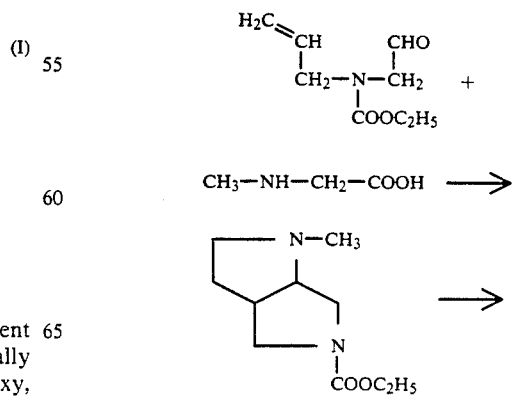

(II)          (III)

(I) + $CO_2$ + $H_2O$ in which R' represents H or $C_1$-$C_3$-alkyl and where $R^1$-$R^6$ have the abovementioned meanings The substituents $R^2$ or $R^6$, which have a protective group function, can then be removed.

The advantage of the process according to the invention consists in the simplicity of carrying it out and in the easy availability of the starting compounds (II) and (III). The high stereoselectivity of the process must be designated as particularly advantageous. This is particularly surprising since similar cyclizations can lead to product mixtures (J. Chem. Soc., Chem. Comm. 1984, 182). Owing to the selectivity of the process claimed here, a high-loss and uneconomical separation of undesired diastereomers is unnecessary.

The course of the reaction of the process according to the invention may be illustrated by the following examples:

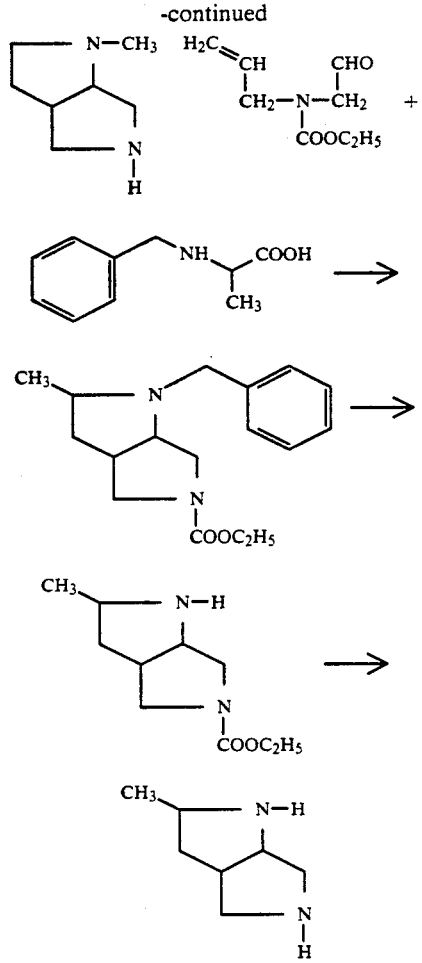

The unsaturated carbonyl compounds of the formula (II) needed as starting compounds are new. They can be prepared by the following methods:

1. Starting from commercially available aminoacetaldehyde dimethyl acetal, the amino group is acylated, the amide is alkylated with allyl halides in the presence of strong bases and the acetal is cleaved under acidic conditions.

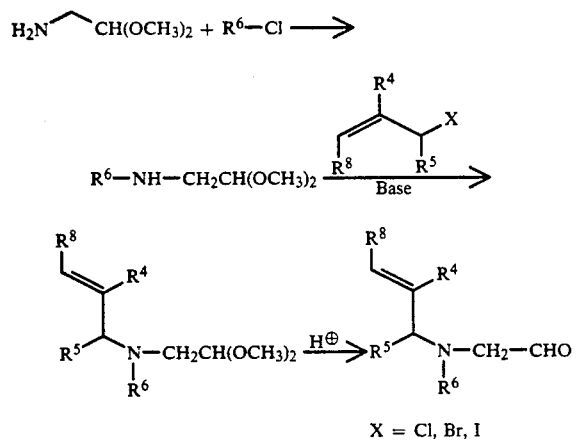

X = Cl, Br, I

The known acetamidoacetone dimethyl acetal (Synthesis 1988, 381) can be alkylated with allyl halides in the presence of strong bases and the acetal group hydrolyzed under acidic conditions.

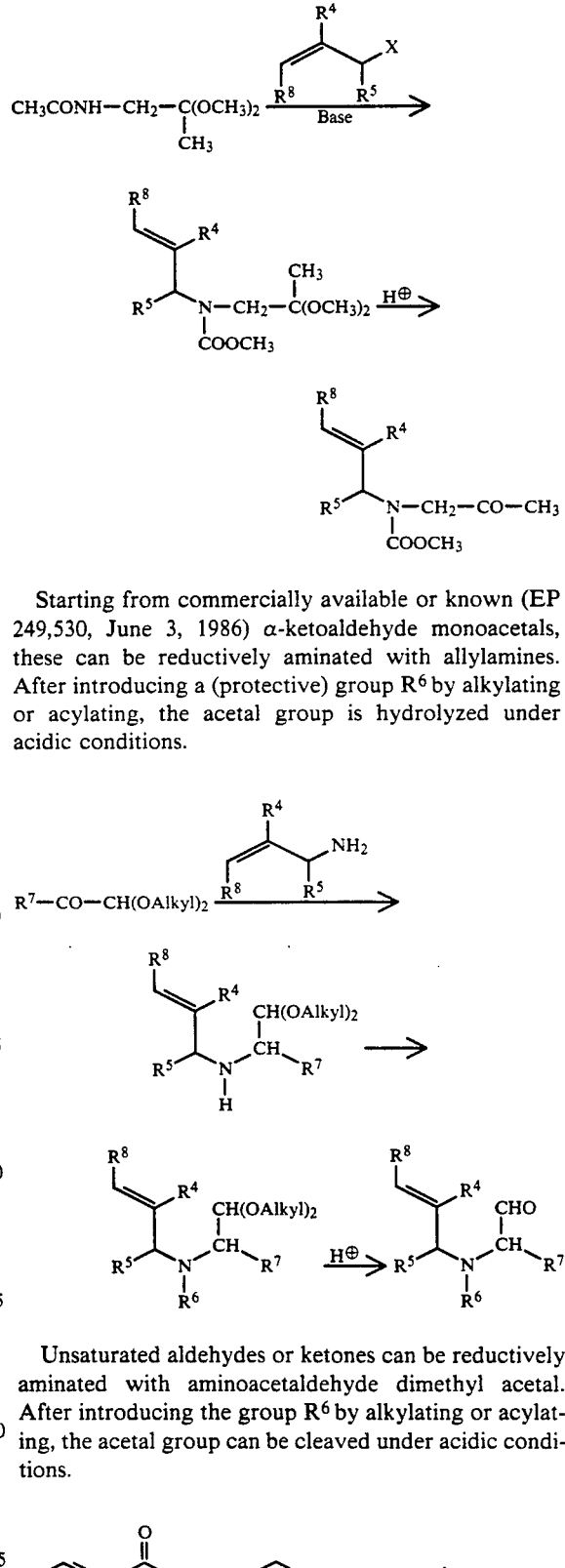

Starting from commercially available or known (EP 249,530, June 3, 1986) α-ketoaldehyde monoacetals, these can be reductively aminated with allylamines. After introducing a (protective) group $R^6$ by alkylating or acylating, the acetal group is hydrolyzed under acidic conditions.

Unsaturated aldehydes or ketones can be reductively aminated with aminoacetaldehyde dimethyl acetal. After introducing the group $R^6$ by alkylating or acylating, the acetal group can be cleaved under acidic conditions.

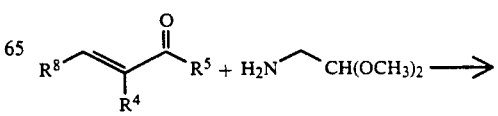

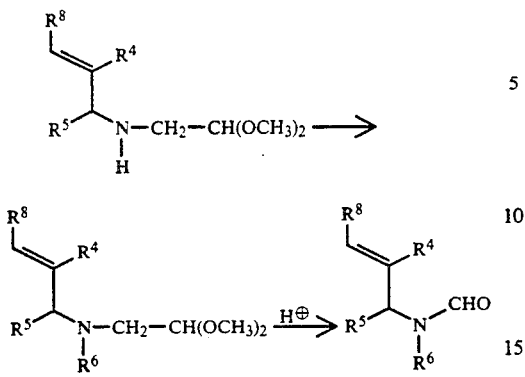

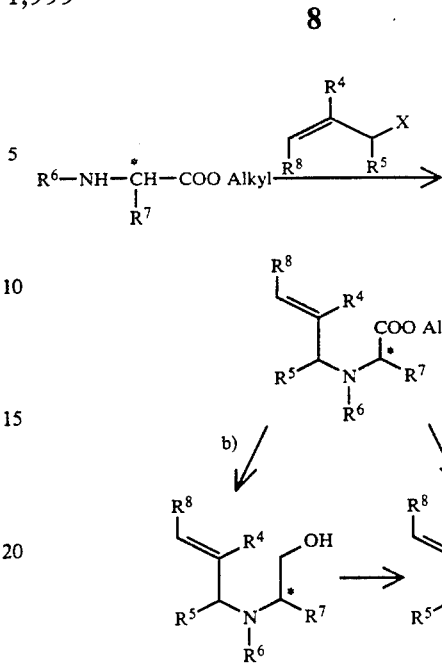

N-Allylamino alcohols are obtained
a) by ring opening of epoxides with allylamindes (J. Pharm. Soc. Japan 73, 1330 (1953)),
b) by alkylating substituted ethanolamines with allyl halides (J. Am. Chem. Soc. 64, 1692 (1942); 72, 3536 ((1950)),
c) by reductive amination of unsaturated aldehydes or ketones with substituted ethanolamines.

After introducing the group $R^6$ by alkylating or acylating, the alcohol function is oxidized with suitable oxidizing agents to give compounds of the formula (II).

Examples of precursors of the formula (II) which may be mentioned are:
methyl N-allyl-N-(2-oxoethyl)-carbamate,
ethyl N-allyl-N-(2-oxoethyl)-carbamate,

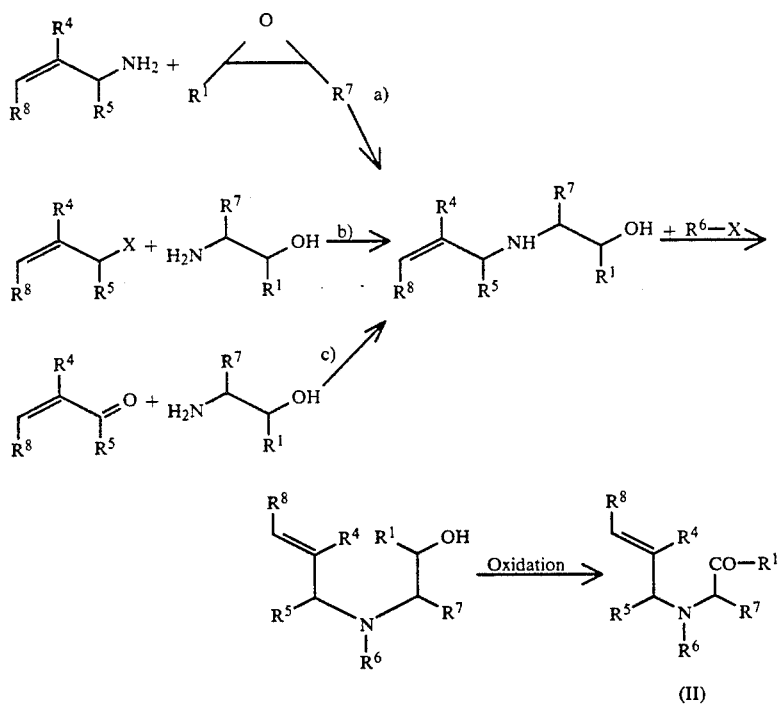

Enantiomerically pure precursors of the formula (II) are obtained by alkylating N-acylated amino acid esters with allyl halides in the presence of strong bases. Using suitable reducing agents, the ester function can be
a) reduced to the aldehyde function or
b) reduced to the alcohol and then oxidized to the aldehyde function using suitable oxidizing agents.

isopropyl N-allyl-N-(2-oxoethyl)-carbamate,
tert.-butyl N-allyl-N-(2-oxoethyl)-carbamate,
N-allyl-N-(2-oxoethyl)-acetamide,
N-allyl-N-(2-oxoethyl)-propionamide,
N-allyl-N-(2-oxoethyl)-benzamide,
methyl N-allyl-N-(1-oxoprop-2-yl)-carbamate,
ethyl N-allyl-N-(1-oxoprop-2-yl)-carbamate,
propyl N-allyl-N-(1-oxoprop-2-yl)-carbamate,
N-allyl-N-(1-oxoprop-2-yl)-acetamide,
N-allyl-N-(1-oxoprop-2-yl)-benzamide, methyl N-(buten-3-yl)-N-(2-oxoethyl)-carbamate,
ethyl N-(buten-3-yl)-N-(2-oxoethyl)-carbamate,
Iisopropyl N-(buten-3-yl)-N-(2-oxoethyl)-carbamate,
tert.-butyl N-(buten-3-yl)-N-(2-oxoethyl)-carbamate,
N-(buten-3-yl)-N-(2-oxoethyl)-acetamide,
N-(buten-3-yl)-N-(2-oxoethyl)-benzamide,
methyl N-(2-methylallyl)-N-(2-oxoethyl)-carbamate,
ethyl N-(2-methylallyl)-N-(2-oxoethyl)-carbamate,
N-(2-methylallyl)-N-(2-oxoethyl)-acetamide,
N-(2-methylallyl)-N-(2-oxoethyl)-benzamide,
methyl N-(2-fluoroallyl)-N-(2-oxoethyl)-carbamate,
ethyl N-(2-fluoroallyl)-N-(2-oxoethyl)-carbamate,
N-(2-fluoroallyl)-N-(2-oxoethyl)-acetamide,
N-(2-fluoroallyl)-N-(2-oxoethyl)-benzamide,
methyl N-(2-chloroallyl)-N-(2-oxoethyl)-carbamate,
ethyl N-(2-chloroallyl)-N-(2-oxoethyl)-carbamate,
N-(2-chloroallyl)-N-(2-oxoethyl)-acetamide,
N-(2-chloroallyl)-N-(2-oxoethyl)-benzamide,
methyl N-(2-bromoallyl)-N-(2-oxoethyl)-carbamate,
ethyl N-(2-bromoallyl)-N-(2-oxoethyl)-carbamate,
N-(2-bromoallyl)-N-(2-oxoethyl)-acetamide,
N-(2-bromoallyl)-N-(2-oxoethyl)-benzamide,
methyl N-(2-ethoxycarbonylallyl)-N-(2-oxoethyl)-carbamate,
ethyl N-(2-ethoxycarbonylallyl)-N-(2-oxoethyl)-carbamate,
N-(2-ethoxycarbonylallyl)-N-(2-oxoethyl)-acetamide,
N-(2-ethoxycarbonylallyl)-N-(2-oxoethyl)-benzamide,
ethyl N-(2-oxoethyl)-N-(2-phenylallyl)-carbamate,
methyl N-(2-buten-1-yl)-N-(2-oxoethyl)-carbamate,
ethyl N-(2-buten-1-yl)-N-(2-oxoethyl)-carbamate,
N-(2-buten-1-yl)-N-(2-oxoethyl)-acetamide,
N-(2-buten-1-yl)-N-(2-oxoethyl)-benzamide,
methyl N-(3-chloroallyl)-N-(2-oxoethyl)-carbamate,
ethyl N-(3-chloroallyl)-N-(2-oxoethyl)-carbamate,
N-(3-chloroallyl)-N-(2-oxoethyl)-acetamide,
N-(3-chloroallyl)-N-(2-oxoethyl)-benzamide,
methyl N-(3-phenylallyl)-N-(2-oxoethyl)-carbamate,
ethyl N-(3-phenylallyl)-N-(2-oxoethyl)-carbamate,
N-(3-phenylallyl)-N-(2-oxoethyl)-acetamide,
N-(3-phenylallyl)-N-(2-oxoethyl)-benzamide,
methyl N-(3-ethoxycarbonylallyl)-N-(2-oxoethyl)-carbamate,
ethyl N-(3-ethoxycarbonylallyl)-N-(2-oxoethyl)-carbamate,
N-(3-ethoxycarbonylallyl)-N-(2-oxoethyl)-acetamide,
ethyl N-allyl-N-(2-oxopropyl)-carbamate,
N-allyl-N-(2-oxopropyl)-acetamide,
N-allyl-N-(2-oxopropyl)-benzamide,
N-allyl-N-(2-oxo-2-phenylethyl)-acetamide,
N-allyl-N-(2-ethoxycarbonyl-2-oxoethyl)-acetamide,
N-allyl-N-benzyl-N-2-(oxopropyl)-amine,
N-benzyl-N-(2-methylallyl)-N-(2-oxoethyl)-amine.

The starting compounds of the formula (III) are known from the literature and are, for the most part, commercially available.

Examples of precursors of the formula (III) which may be mentioned are: sarcosine, N-ethylglycine, N-propy.glycine, N-isopropylglycine, N-phenylglycine, N-benzylglycine, N-methylalanine, N-phenylalanine, N-methylphenylglycine, N-benzylphenylglycine, azetidine-2-carboxylic acid, proline, trans-4-hydroxyproline, piperidine-2-carboxylic acid, thiazolidine-4-carboxylic acid, 5,5-dimethylthiazolidine-4-carboxylic acid, sarcosine methyl ester, sarcosine ethyl ester, N-benzylglycine methyl ester and N-benzylglycine ethyl ester.

The reaction of (II) with (III) by the process according to the invention is carried out in a solvent. Hydrocarbons such as benzene, toluene, xylenes or tetralin, ethers such as dioxane, dibutyl ether, dimethoxyethane, diethylene glycol dimethyl ether, diethylene glycol diethyl ether, alcohols such as butanol, pentanol, ethylene glycol, ethylene glycol monomethyl ether and ethylene glycol monoethyl ether, and dipolar aprotic solvents such as dimethylformamide, dimethyl sulphoxide, N-methylpyrrolidone and sulpholane can be used. Toluene, xylenes and dimethylformamide are particularly preferred.

The reaction temperature can be varied within a relatively wide range. In general, the reactions are carried out between 20° C. and 200° C., preferably between 80° C. and 150° C.

The reaction can be carried out at normal pressure, but also at elevated pressure. In general, the reaction is carried out at pressures between about 1 bar and 100 bar, preferably between about 1 bar and 10 bar.

When carrying out the process according to the invention, 0.5 to 6 moles, preferably 0.5 to 2 moles, of amino acid derivative (III) are employed per mole of unsaturated carbonyl compound (II).

The reaction can be carried out by adding the unsaturated carbonyl compound dropwise to a suspension or solution of the amino acid derivative (III) in one of the solvents indicated. However, both components can also be initially introduced in a solvent and the reaction can be carried out in the temperature range indicated. The water of reaction set free in the reaction can be distilled off with the solvent as an azeotrope. The course of the reaction can easily be followed by the evolution of $CO_2$ which occurs. Working up is carried out, if appropriate after separating off unreacted amino acid (III), by removing the solvent and distillation. It is also possible to extract the basic products from the organic solvent using an acid, such as, for example hydrochloric acid, in order to separate off neutral impurities.

In a further step of the process according to the invention, the substituents $R^2$ and $R^6$, if they have a protective group function, can be removed.

Acyl radicals are removed by hydrolysis. Strong acids or strong bases are suitable for the hydrolysis. Aqueous hydrochloric acid, hydrobromic acid or trifluoroacetic acid are preferably used for the acidic hydrolysis. The basic hydrolysis is carried out using alkali metal hydroxides or alkaline earth metal hydroxides, lithium hydroxide, sodium hydroxide, potassium hydroxide, calcium hydroxide and barium hydroxide being preferred. Solvents used are water and alcohols, water, ethanol or mixtures of these solvents being preferred. The hydrolysis can be carried out at temperatures between 0° and 200° C., preferably between 20° and 140° C. Pressures between about 1 bar and 100 bar are used here, preferably between about 1 bar and 10 bar.

If the radicals $R^2$ or $R^6$ are benzyl radicals, these radicals can be removed by hydrogenolysis. Water, alcohols, carboxylic acids, alcoholic hydrochloric acid, cyclic ethers or mixtures thereof can be used as solvents. Catalysts used are palladium, both as a sponge and on supports such as active carbon, calcium carbonate or barium sulphate, and palladium hydroxide on active carbon. The reaction is carried out at temperatures between about 0° and 200° and hydrogen pressures from 1 bar to 200 bar.

The process according to the invention moreover comprises the conversion of the radicals $R^2$ and $R^{6,}$ if these are acyl radicals, into alkyl radicals by reduction. The reduction can be carried out both catalytically and using hydrides or complex hydrides of the elements of the third main group. The reduction is preferably carried out using diborane, lithium aluminum hydride and sodium borohydride, in the last case with the addition of Lewis acids such as titanium tetrachloride, aluminum trichloride or boron trifluoride.

The reaction is carried out in inert organic solvents such as ethers, for example diethyl ether, dibutyl ether, methyl tert.-butyl ether, tetrahydrofuran, dioxane or ethylene glycol dimethyl ether or hydrocarbons such as toluene or xylene. The temperatures can be varied between about 0° and 200° C. In order to attain high reaction temperatures, the reaction can be carried out at pressures up to 100 bar.

Preferably, the reduction is carried out using lithium aluminum hydride or sodium borohydride/boron trifluoride etherate in tetrahydrofuran or dioxane at the reflux temperature of the solvent.

The compounds according to the invention are used as starting substances for antibacterially active quinolone- or naphthyridonecarboxylic acids.

Thus, for example, 8-chloro-1-cyclopropyl-6,7-difluoro-1,4-dihydro-4-oxo-3-quinolinecarboxylicacid can be reacted with 2-methyl-2,7-diazabicyclo[3.3.0]octane to give 8-chloro-1-cyclopropyl-6-fluoro-1,4-dihydro-7-(2-methyl-2,7-diazabicyclo[3.3.0]oct-7-yl)-4-oxo-3-quinolinecarboxylic acid, which has a high antibacterial activity.

EXAMPLE 1

2,7-Diazabicyclo[3.3.0]octane a) Ethyl N-(2,2-dimethoxyethyl)-carbamate
$H_5C_2OOC-NH-CH_2-CH(OCH_3)_2$ 214 g (2 mol) of ethyl chloroformate are added dropwise at 10° C. to 214 g (2 mol) of aminoacetaldehyde dimethyl acetal in 1 l of toluene and 90 g of NaOH in 500 ml of water. The mixture is stirred for a further 2 hours at room temperature, and the aqueous phase is separated off, saturated with sodium chloride and extracted using toluene. The toluene solutions are dried over magnesium sulphate, concentrated and distilled.

Yield: 338 g (95.4% of theory).
Boiling point: 60° C./0.03 mbar.

b) Ethyl N-allyl-N-(2,2-dimethoxyethyl)-carbamate

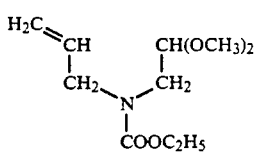

500 g (2.82 mol) of ethyl N-(2,2-dimethoxyethyl)carbamate, 625 g of powdered potassium hydroxide and 10 g of triethylbenzylammonium chloride are initially introduced into 2.7 l of toluene and 345 g (2.85 mol) of allyl bromide are added dropwise at room temperature. The mixture is stirred overnight at room temperature, the salts are filtered off with suction, and the filtrate is washed once with saturated sodium chloride solution, dried over potassium carbonate, concentrated and distilled.

Yield: 582 g (95% of theory).
Boiling point: 64° C./0.1 mbar.

c) Ethyl N-allyl-N-(2-oxoethyl)-carbamate

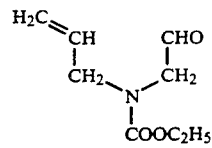

68 g (0.313 mol) of ethyl N-allyl-N-(2,2-dimethoxyethyl) -carbamate are heated at 100° C. for an hour with 150 ml of formic acid. The mixture is poured onto ice, extracted several times with methylene chloride, and the organic phases are washed with sodium hydrogen carbonate solution, dried over magnesium sulphate, concentrated and distilled.

Yield: 46.7 g (87.2% of theory).
Boiling point: 58° C./0.09 mbar.

d) N-Benzylglycine

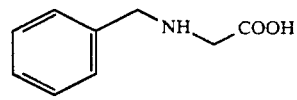

225.8 g (1.17 mol) of N-benzylglycine ethyl ester (J. Am. Chem. Soc. 72, 1238 (1950)) are heated under reflux overnight in 600 ml of water. Product which has crystallized out is filtered off with suction and the filtrate is extracted once with tert.-butyl methyl ether. The aqueous phase is concentrated and the crystals obtained are dried over phosphorus pentoxide in a desiccator together with the product filtered off.

Yield: 184 g (95% of theory).
Melting point: 199° C.

e) Ethyl 2-benzyl-2,7-diazabicyclo[3.3.0]octane-7-carboxylate

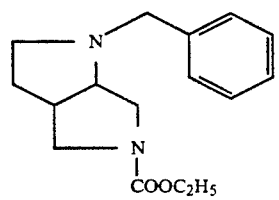

42.8 g (0.25 mol) of ethyl N-allyl-N-(2-oxoethyl) -carbamate are heated under reflux overnight with 41.3 g (0.25 mol) of N-benzylglycine in 750 ml of toluene. The mixture is concentrated and the residue is distilled.

Yield: 59.6 g (87% of theory).
Boiling point: 140° C./0.09 mbar.

f) Ethyl 2,7-diazabicyclo[3.3.0]octane-7-carboxylate

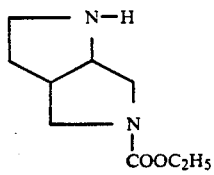

21.2 g (77.3 mmol) of ethyl 2-benzyl-2,7-diazabicyclo[3.3.0]octane-7-carboxylate in 400 ml of ethanol are hydrogenated at 100° C. and 100 bar on 3 g of palladium-active carbon (10% Pd). The catalyst is filtered off, the filtrate is concentrated and the residue is distilled.

Yield: 10.3 g (72.3% of theory).
Boiling point: 82–92° C./0.1 mbar.

g) 2,7-Diazabicyclo[3.3.0]octane

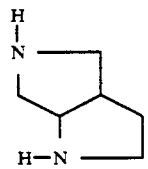

9 g (48.8 mmol) of ethyl 2,7-diazabicyclo[3.3.0]-octane-7-carboxylate are heated under reflux overnight with 32 g (100 mmol) of Ba(OH)$_2$.8H$_2$O in 140 ml of water. The mixture is saturated with potassium carbonate, barium carbonate is filtered off with suction and the filtrate is extracted ten times with 100 ml of chloroform each time. The extract is dried over potassium carbonate and concentrated, and the residue is distilled.

Yield: 3.4 g (62% of theory).
Boiling point: 70° C./6 mbar.

EXAMPLE 2

2-Benzyl-2,7-diazabicyclo[3.3.0]octane

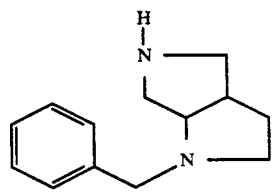

55.6 g (0.2 mol) of ethyl 2-benzyl-2,7-diazabicyclo[3.3.0]octane-7-carboxylate are heated under reflux overnight with 300 ml of concentrated hydrochloric acid. The mixture is then rendered alkaline with potassium carbonate and extracted five times with 100 ml of chloroform each time, the extracts are dried over potassium carbonate and concentrated, and the residue is distilled.

Yield: 31 g (76.6% of theory).
Boiling point: 105° C./0.45 mbar.

EXAMPLE 3

Ethyl 2,7-diazabicyclo[3.3.0]octane-2-carboxylate a) tert.-Butyl 2-benzyldiazabicyclo[3.3.0]octane-7-carboxylate

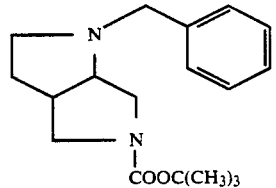

20.2 g (0.1 mol) of 2-benzyl-2,7-diazabicyclo-[3.3.0]octane are dissolved in 125 ml of tert.-butanol, a solution of 4.2 g of sodium hydroxide in 100 ml of water is added and 23 g (0.105 mol) of di-tert.-butyl pyrocarbonate are added dropwise at room temperature. The mixture is stirred overnight at room temperature and extracted five times with 100 ml of chloroform each time, the extracts are dried over potassium carbonate and concentrated, and the residue is distilled.

Yield: 24.8 g (82% of theory).
Boiling point: 145–149° C./0.8 mbar.

b) tert.-Butyl 2,7-diazabicyclo[3.3.0]octane-7-carboxylate

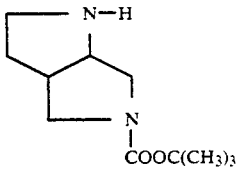

24 g (79.4 mmol) of tert.-butyl 2-benzyldiazabicyclo [3.3.0]octane-7-carboxylate in 400 ml of ethanol are hydrogenated at 100° C. and 100 bar on 3 g of palladium-active carbon (10% Pd). The catalyst is filtered off, the filtrate is concentrated and the residue is distilled.

Yield: 13.1 g (77.7% of theory).
Boiling point: 87° C./0.1 mbar.

c) 2-Ethyl7-tert.-butyl2,7-diazabicyclo[3.3.0]octane-2,7-dicarboxylate

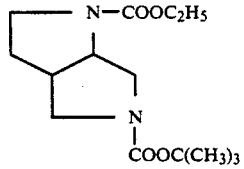

13 g (61.2 mmol) of tert.-butyl 2,7-diazabicyclo-[3.3.0]octane-7-carboxylate are dissolved in 100 ml of toluene, a solution of 3 g of sodium hydroxide in 20 ml of water is added and 7 g (64.5 mmol) of ethyl chloroformate are added dropwise at room temperature. The mixture is stirred for three hours at room temperature, and the aqueous phase is separated off and extracted twice with 100 ml of methylene chloride each time. The organic solutions are dried over magnesium sulphate and concentrated, and the residue is distilled.

Yield: 16 g (91.9% of theory).

d) Ethyl 2,7-diazabicyclo[3.3.0]octane-2-carboxylate

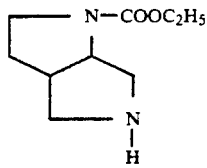

15.2 g (53.5 mmol) of 2-ethyl 7-tert.-butyl 2,7-diazabicyclo[3.3.0]octane-2,7-dicarboxylate in 100 ml of chloroform are heated under reflux for five hours with 10.5 g (55.3 mol) of para-toluenesulphonic acid. The mixture is washed with 50 ml of 10% strength sodium hydroxide solution, the organic phase is dried over potassium carbonate and concentrated, and the residue is distilled.
Yield: 9.5 g (96.4% of theory).
Boiling point: 80-90° C./0.1 mbar.

EXAMPLE 4

2-Methyl-2,7-diazabicyclo[3.3.0]octane a) Ethyl 2-methyl-2,7-diazabicyclo[3.3.0]octane-7-carboxylate

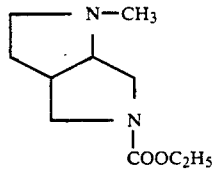

8.6 g (50 mmol) of ethyl N-allyl-N-(2-oxoethyl)-carbamate are heated under reflux overnight with 4.5 g (50 mmol) of sarcosine in 200 ml of toluene. The mixture is concentrated and the residue is distilled.
Yield: 7.5 g (75.7% of theory).
Boiling point: 80-82° C./0.1 mbar.

b) 2-Methyl-2,7-diazabicyclo[3.3.0]octane

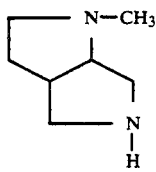

9 g (45.4 mmol) of ethyl 2-methyl-2,7-diazabicyclo[3.3.0]octane-7-carboxylate are heated under reflux overnight with 50 ml of concentrated hydrochloric acid. The mixture is rendered alkaline with potassium carbonate, extracted ten times using 50 ml of chloroform each time, dried over potassium carbonate and concentrated, and the residue is distilled.
Yield: 4.5 g (78% of theory).
Boiling point: 72° C./25 mbar.

EXAMPLE 5

2-Phenyl-2,7-diazabicyclo[3.3.0]octane a) Ethyl 2-phenyl-2,7-diazabicyclo[3.3.0]octane-7-carboxylate

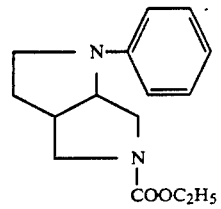

8.6 g (50 mmol) of ethyl N-allyl-N-(2-oxoethyl)-carbamate and 7.6 50 mmol) of phenylglycine are heated under reflux overnight in 200 ml of toluene. The mixture is decanted from resinous material and concentrated, and the residue is distilled.
Yield: 8.1 g (62.2% of theory).
Boiling point: 151° C./0.12 mbar.

b) 2-Phenyl-2,7-diazabicyclo[3.3.0]octane

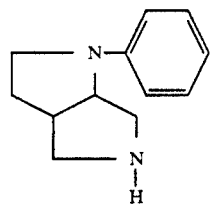

7.6 g (31.6 mmol) of ethyl 2-phenyl-2,7-diazabicyclo[3.3.0]octane-7-carboxylate are heated under reflux overnight with 50 ml of concentrated hydrochloric acid. The mixture is concentrated, the residue is taken up in 50 ml of 10% strength sodium hydroxide solution and the mixture is extracted five times using 50 ml of chloroform each time. The extracts are dried over potassium carbonate and concentrated, and the residue is distilled.
Yield: 3.7 g (62% of theory).
Boiling point: 103° C./0.08 mbar.

EXAMPLE 6

3-Methyl-2,7-diazabicyclo[3.3.0]octane a) N-Benzylalanine

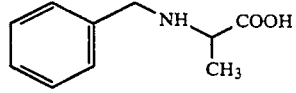

333 g (1.72 mmol) of N-benzylalanine methyl ester (J. Chem. Soc. 4374 (1952)) are heated under reflux overnight with 860 ml of water. Product which has deposited is filtered off with suction and the filtrate is extracted once with tert.-butyl methyl ether. The aqueous solution is concentrated and the crystals obtained are dried over phosphorus pentoxide in a desiccator with the first crystal fraction.
Yield 280 g (91% of theory).
Melting point: 270-276° C. (decomposition).

b) Ethyl 2-benzyl-3-methyl-2,7-diazabicyclo[3.3.0]-octane-7-carboxylate

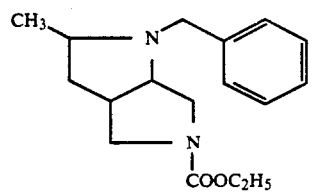

42.8 g (0.25 mol) of ethyl N-allyl-N-(2-oxo -ethyl)-carbamate are heated under reflux overnight with 44.8 g (0.25 mol) of N-benzylalanine in 750 ml of toluene. The mixture is concentrated and the residue is distilled twice.

Yield: 32 g (44.4% of theory).
Boiling point: 128–133° C./0.06 mbar.
The product consists to 96% of a stereoisomer.

c) Ethyl 3-methyl-2,7-diazabicyclo[3.3.0]octane-7-carboxylate

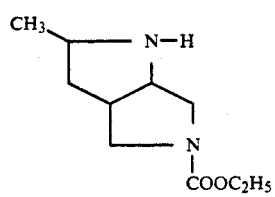

32 g (0.11 mol) of ethyl 2-benzyl-3-methyl-2,7-diazabicyclo[3.3.0]octane-7-carboxylate in 560 ml of ethanol are hydrogenated at 100° C. and 100 bar on 4.5 g of palladium-active carbon. The catalyst is filtered off with suction, the filtrate is concentrated and the residue is distilled.

Yield: 17.1 g (77.7% of theory).
Boiling point: 140–145° C./8 mbar.

d) 3-Methyl-2,7-diazabicyclo[3.3.0]octane

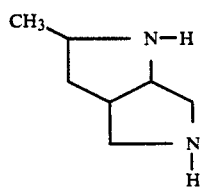

17 g (85.7 mmol) of ethyl .3-methyl-2,7-diazabicyclo[3.3.0]octane-7-carboxylate are heated under reflux overnight with 100 ml of concentrated hydrochloric acid. The mixture is concentrated, the residue is taken up in 50 ml of water, rendered alkaline with potassium carbonate and extracted ten times using 50 ml of chloroform each time. The extracts are dried over potassium carbonate and concentrated, and the residue is distilled.

Yield: 6 g (55% of theory).
Boiling point: 68–70° C./6 mbar.

EXAMPLE 7
2,3-Dimethyl-2,7-diazabicyclo[3.3.0]octane a) Ethyl 2,3-dimethyl-2,7-diazabicyclo[3.3.0]octane-7-carboxylate

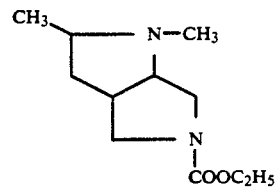

17.2 g (0.1 mol) of ethyl N-allyl-N-(2-oxoethyl) -carbamate are heated under reflux overnight with 10.5 g (0.1 mol) of N-methylalanine in 300 ml of toluene. The mixture is concentrated and the residue is distilled.

Yield: 11.3 g (53.2% of theory).
Boiling point: 81° C./0.25 mbar.

b) 2,3-Dimethyl-2,7-diazabicyclo[3.3.0]octane

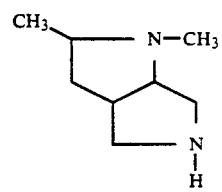

7.25 g (34.2 mmol) of ethyl 2,3-dimethyl-2,7-diazabicyclo[3.3.0]octane-7-carboxylate are heated under reflux overnight with 50 ml of concentrated hydrochloric acid. The mixture is rendered alkaline with potassium carbonate and extracted ten times using 50 ml of chloroform each time, the extracts are dried over potassium carbonate and concentrated, and the residue is distilled.

Yield: 3 g (62.5% of theory).
Boiling point: 72–74° C./10 mbar.

EXAMPLE 8
2,8-Dimethyl-2,7-diazabicyclo[3.3.0]octane a) Ethyl N-(1,1-dimethoxyprop-2-yl)-carbamate

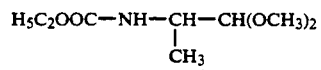

80 g (0.73 mol) of ethyl chloroformate are added dropwise with ice-cooling to 86.2 g (0.72 mol) of 2-aminopropionaldehyde dimethyl acetal in 350 ml of toluene and 32 g (0.8 mol) of NaOH in 300 ml of water. The mixture is stirred for a further 2 hours at room temperature, the organic phase is separated off, the aqueous phase is extracted using toluene and the toluene solutions are dried over K₂CO₃. The extracts are concentrated and the residue is distilled.

Yield: 132 g (95% of theory).
Boiling point: 55° C./0.06 mbar.

b) Ethyl N-allyl-N-(1,1-dimethoxyprop-2-yl)-carbamate

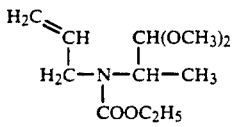

151 g (0.79 mol) of ethyl N-(1,1-dimethoxyprop 2-yl)-carbamate, 175 g of powdered potassium hydroxide and 2.8 g of triethylbenzylammonium chloride are initially introduced into 750 ml of toluene and 94 g (0.777 mol) of allyl bromide are added dropwise at room temperature. After stirring overnight at room temperature, a further 10 g (82.6 mmol) of allyl bromide are added dropwise and the mixture is stirred for one day at room temperature. Water is added until all salts have gone into solution, and the aqueous phase is separated off and extracted twice with 150 ml of toluene each time. The extracts are dried over $K_2CO_3$ and concentrated, and the residue is distilled.

Yield: 173 g (94.7% of theory).
Boiling point: 68° C./0.1 mbar.

c) Allyl-(1,1-dimethoxyprop-2-yl)-amine

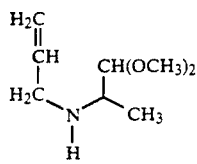

20 g of molecular sieve are added to 12 g (0.1 mol) of 1,1-dimethoxyacetone in 100 ml of ethanol and 7 g (0.12 mol) of allylamine are then added dropwise. The mixture is allowed to stand overnight at room temperature, decanted from the molecular sieve and cooled in an ice-bath to 0° C., and 4 g (0.1 mol) of sodium borohydride are added in small portions. The mixture is stirred overnight at room temperature and concentrated, the residue is taken up in 100 ml of water, and the mixture is saturated with potassium carbonate and extracted five times with 100 ml of chloroform each time. The extracts are dried over potassium carbonate and concentrated, and the residue is distilled.

Yield: 10.3 g (64.7% of theory).
Boiling point: 75° C./25 mbar.

d) Ethyl N-allyl-N-(1,1-dimethoxyprop-2-yl)-carbamate

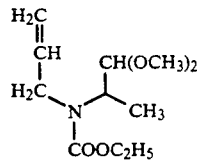

125 g (0.785 mol) of allyl-(1,1-dimethoxyprop-2-yl)amine are initially introduced into 400 ml of toluene, a solution of 40 g of sodium hydroxide in 200 ml of water is added, the mixture is cooled in an ice-bath to 0° C. and 95 g (0.876 mol) of ethyl chloroformate are added dropwise. The mixture is then stirred for 3 hours at room temperature, and the aqueous phase is separated off and extracted twice using 100 ml of toluene each time. The extracts are dried over potassium carbonate and concentrated, and the residue is distilled.

Yield: 170.8 g (94% of theory).
Boiling point: 55° C./0 05 mbar.

e) Ethyl N-allyl-N-(1-oxoprop-2-yl)-carbamate

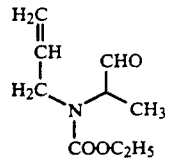

182 g (0.7S7 mol) of ethyl N-allyl-N-(1,1-dimethoxyprop-2-yl)-carbamate in 1.5 l of water are heated under reflux for three hours with 80 ml of formic acid. The mixture is saturated with sodium chloride, the organic phase is separated off and the aqueous phase is extracted twice with 500 ml of methylene chloride each time. The organic solutions are washed with saturated sodium hydrogen carbonate solution until neutral, dried over magnesium sulphate and concentrated, and the residue is distilled.

Yield: 134 g (91.9% of theory).
Boiling point: 65 C/0.23 mbar.

f) Ethyl 2,8-dimethyl-2,7-diazabicyclo[3.3.0]octane-7-carboxylate

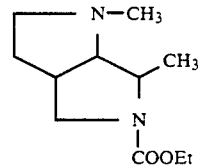

18.5 g (0.1 mol) of ethyl N-allyl-N-(1-oxoprop -2-yl)-carbamate are heated under reflux overnight in a water separator with 9 g (0.1 mol) of sarcosine in 300 ml of toluene. The mixture is concentrated and the residue is distilled.

Yield: 17 g (80% of theory).
Boiling point: 140–150° C./8 mbar.

g) 2,8-Dimethyl-2,7-diazabicyclo[3.3.0]octane

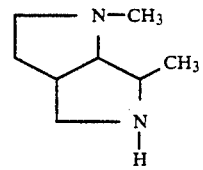

16.9 g (79.6 mol) of ethyl 2,8-dimethyl-2,7-diazabicyclo[3.3.0]octane-7-carboxylate are heated under reflux overnight with 130 ml of concentrated hydrochloric acid. The mixture is concentrated, the residue is taken up in 50 ml of water, and the mixture is rendered alkaline with potassium carbonate and extracted five times using 50 ml of chloroform each time. The extracts are dried over potassium carbonate and concentrated, and the residue is distilled.

Yield: 6.6 g (58.5% of theory).
Boiling point: 60–62° C./6 mbar.

EXAMPLE 9

5-Chloro-2-methyl-2,7-diazabicyclo[3.3.0]octane a) Ethyl N-(2-chloroallyl)-N-(2,2-dimethoxyethyl)-carbamate

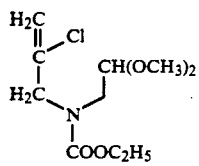

115 g (0.65 mol) of ethyl N-(2,2-dimethoxyethyl)-carbamate, 130 g of powdered potassium hydroxide and 2 g of triethylbenzylammonium chloride are initially introduced into 650 ml of toluene and 142 g (0.7 mol) of 2-chloroallyl iodide are added dropwise at room temperature. After stirring overnight, a gas chromatogram showed incomplete conversion, hence 65 g of powdered potassium hydroxide and 1 g of triethylbenzylammonium chloride were added again and a further 71 g (0.35 mol) of 2-chloroallyl iodide were added dropwise. After stirring overnight at room temperature, the salts were filtered off with suction, the filtrate was washed with saturated sodium chloride solution, dried over magnesium sulphate and concentrated, and the residue was distilled.

Yield: 140.9 g (86% of theory).
Boiling point: 92-97° C./0.8 mbar.

b) Ethyl N-(2-chloroallyl)-N-(2-oxoethyl)-carbamate

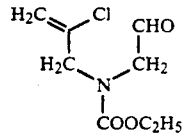

151 g (0.6 mol) of ethyl N-(2-chloroallyl)-N -(2,2-dimethoxyethyl)-carbamate are heated under reflux for 3 hours with 60 ml of formic acid in 1.2 l of water. The mixture is saturated with sodium chloride, and the aqueous phase is separated off and extracted twice with 300 ml of methylene chloride each time. The organic phases are washed with saturated sodium hydrogen carbonate solution until neutral, dried over magnesium sulphate and concentrated, and the residue is distilled.

Yield: 97.1 g (78% of theory).
Boiling point: 88-91° C./0.06 mbar.

c) Ethyl 5-chloro-2-methyl-2,7-diazabicyclo[3.3.0]-octane-7-carboxylate

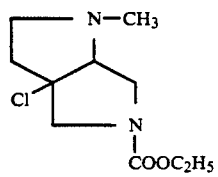

10.3 g (50mmol) of ethyl N-(2-chloroallyl)-N-(2-oxoethyl)-carbamate are heated under reflux overnight with 4.5 g (50 mmol) of sarcosine in 200 ml of toluene. The mixture is concentrated and the residue is distilled.

Yield: 10.6 g (91% of theory).
Boiling point: 80° C./0.1 mbar.

d) 5-Chloro-2-methyl-2,7-diazabicyclo[3.3.01]octane

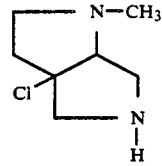

9.3 g (40 mmol) of ethyl 5-chloro-2-methyl-2,7-diazabicyclo[3.3.0]octane-7-carboxylate are heated under reflux overnight with 50 ml of concentrated hydrochloric acid. The mixture is concentrated, the residue is taken up in 30 ml of water, and the mixture is rendered alkaline with potassium carbonate and extracted five times with 50 ml of chloroform each time. The extracts are dried over potassium carbonate and concentrated, and the residue is distilled.

Yield: 4.7 g (72% of theory).
Boiling point: 73° C./4 mbar.

EXAMPLE 10

5-Chloro-2,3-dimethyl-2,7-diazabicyclo[3.3.0]octane a) Ethyl 5-chloro-2,3-dimethyl-2,7-diazabicyclo[3.3.0]-octane-7-carboxylate

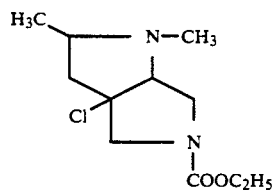

10.3 g (50 mmol) of ethyl N-(2-chloroallyl)-N-(2 -oxoethyl)-carbamate are heated under reflux overnight with 5.2 g (50.5 mmol) of N-methylalanine in 200 ml of toluene. The mixture is concentrated and the residue is distilled.

Yield: 8.1 g (65.7% of theory).
Boiling point: 87° C./0.08 mbar.

b) 5-Chloro-2,3-dimethyl-2,7-diazabicyclo[3.3.0]octane

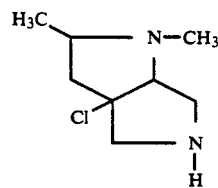

7.6 g (30.8 mmol) of ethyl 5-chloro-2,3-dimethyl -2,7-diazabicyclo[3.3.0]octane-7-carboxylate are heated under reflux overnight with 30 ml of concentrated hydrochloric acid. The mixture is concentrated, the residue is taken up in 30 ml of water, and the mixture is rendered alkaline with potassium carbonate, extracted five times with 50 ml of chloroform each time, dried over potassium carbonate and concentrated, and the residue is distilled.

Yield: 3.7 g (68.4% of theory).

Boiling point: 95-97° C./6 mbar.

EXAMPLE 11

1,4-Diazatricyclo[6.2.0.0$^{2,6}$]decane a) Ethyl 1,4-diazatricyclo[6.2.0.0$^{2,6}$]decane-4-carboxylate

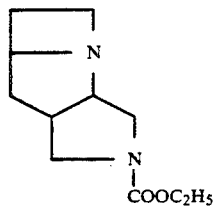

17.1 g (0.1 mol) of ethyl N-allyl-N-(2-oxoethyl) -carbamate are heated under reflux overnight in a water separator with 10 g (0.1 mol) of azetidine-2-carboxylic acid in 200 ml of toluene. Unreacted amino acid is filtered off with suction, the filtrate is concentrated and the residue is distilled.

Yield: 13.8 g (65.6% of theory).
Boiling point: 108° C./0.35 mbar.

b) 1,4-Diazatricyclo[6.2.0.0$^{2,6}$]decane

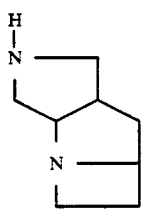

13.7 g (65.1 mmol) of ethyl 1,4-diazatricyclo [6.2.0.0$^{2,6}$]decane-4-carboxylate are heated under reflux overnight with 42 g of Ba(OH)$_2$.8H$_2$O in 150 ml of water. Potassium carbonate is added, barium carbonate is filtered off with suction and the filtrate is extracted ten times using 100 ml of chloroform each time. The extracts are dried over potassium carbonate and concentrated, and the residue is distilled.

Yield: 5.3 g (58.9% of theory).
Boiling point: 85° C./6 mbar.

EXAMPLE 12

1,4-Diazatricyclo[6.3.0.0$^{2,6}$]undecane a) Ethyl 1,4-diazatricyclo[6.3.0.0$^{2,6}$]undecane-4-carboxylate

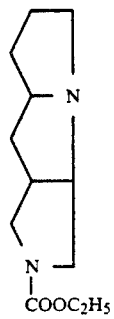

8.6 g (50 mmol) of ethyl N-allyl-N-(2-oxoethyl) -carbamate are heated under reflux overnight with 5.8 g (50 mmol) of proline in 200 ml of toluene. The mixture is concentrated and the residue is distilled.

Yield: 9.6 g (86% of theory).
Boiling point: 102-112° C./0.13-0.15 mbar.

b) 1,4-Diazatricyclo[6.3.0.0$^{2,5}$]undecane

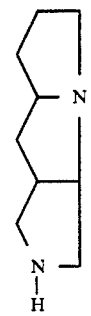

9 g (40 mmol) of ethyl 1,4-diazatricyclo-[6.3.0.0$^{2,6}$]undecane-4-carboxylate are heated under reflux overnight with 50 ml of concentrated hydrochloric acid. The mixture is rendered alkaline with potassium carbonate and extracted ten times using 50 ml of chloroform each time, the extracts are dried over potassium carbonate and concentrated, and the residue is distilled.

Yield: 4.9 g (80.5% of theory).
Boiling point: 50° C./0.05 mbar.

EXAMPLE 13

10-Hydroxy-1,4-diazatricyclo[6.3.0.0$^{2,6}$]undecane a) Ethyl 10-hydroxy-1,4-diazatricyclo[6.3.0.0$^{2,6}$]-undecane-4-carboxylate

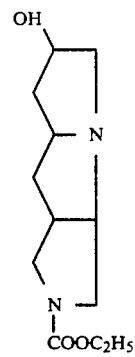

8.6 g (50 mmol) of ethyl N-allyl-N-(2-oxoethyl) -carbamate are heated at 120° C. overnight with 6.6 g (50 mmol) of trans-4-hydroxyproline in 200 ml of dimethylformamide. The mixture is concentrated and the residue is distilled.

Yield: 9.7 g (81% of theory).
Boiling point: 170° C./0.3 mbar.

The product consists predominantly of two stereoisomers in the ratio 1:1.

b) 10-Hydroxy-1,4-diazatricyclo[6.3.0.0²,⁶]undecane

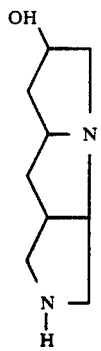

8 g (33.3 mmol) of ethyl 10-hydroxy-1,4-diazatricyclo[6.3.0.0²,⁶]undecane-4-carboxylate are heated under reflux overnight with 21 g of Ba(OH)₂.8H₂O in 150 ml of water. The mixture is saturated with potassium carbonate, barium carbonate is filtered off with suction and the filtrate is extracted ten times using 100 ml of chloroform each time. The extracts are dried over potassium carbonate and concentrated, and the residue is distilled.
Yield: 4.6 g (82% of theory).
Boiling point: 110–115° C./0 1 mbar.

EXAMPLE 14

1,4-Diazatricyclo[6.4.0.0²,⁶]dodecane a) Ethyl 1,4-diazatricyclo[6.4.0.0²,⁶]dodecane-4-carboxylate

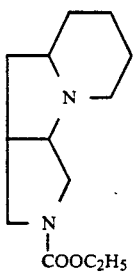

17.1 g (0.1 mol) of ethyl N-allyl-N-(2-oxoethyl) -carbamate are heated under reflux overnight with 13 g (0.1 mol) of piperidine-2-carboxylic acid in 200 ml of toluene. The mixture is concentrated and the residue is distilled.
Yield: 20.8 g (87.2% of theory).
Boiling point: 105–112° C./0.12 mbar.

b) 1,4-Diazatricyclo[6.4.0.0²,⁶]decane

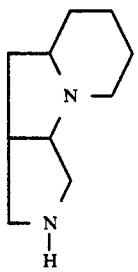

20.7 g (86.8 mmol) of ethyl 1,4-diazatricyclo-[6.4.0.0²,⁶]dodecane-4-carboxylate are heated under reflux overnight with 250 ml of concentrated hydrochloric acid. The mixture is concentrated, the residue is taken up in 50 ml of water and the mixture is rendered alkaline with potassium carbonate. It is extracted ten times using 50 ml of chloroform each time, the extracts are dried over potassium carbonate and concentrated, and the residue is distilled.
Yield: 8.5 g (58.9% of theory).
Boiling point: 108° C./8 mbar.

EXAMPLE 15

10-Thia-1,4-diazatricyclo[6.3.0.0²,⁶]undecane a) Ethyl 10-thia-1,4-diazatricyclo[6.3.0.0²,⁶]undecane-4-carboxylate

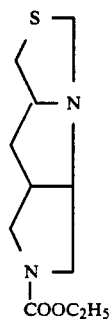

17.2 g (0.1 mol) of ethyl N-allyl-N-(2-oxoethyl) -carbamate are heated under reflux overnight with 13.5 g (0 1 mol) of thiazolidine-4-carboxylic acid in 300 ml of toluene. The mixture is concentrated and the residue is distilled.
Yield: 20 g (82.5% of theory).
Boiling point: 155–156° C./0.5 mbar.

b) 10-Thia-1,4-diazatricyclo[6.3.0.0²,⁶]undecane

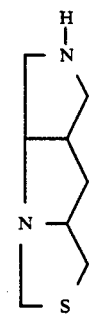

12.5 g (50 mmol) of ethyl 10-thia-1,4-diazatricyolo[6.3.0.0²,⁶]undecane-4-carboxylate are heated under reflux overnight with 32 g of Ba(OH)₂.8H₂O in 225 ml of water. Potassium carbonate is added to the mixture, barium carbonate is filtered off with suction and the filtrate is extracted ten times using 100 ml of chloroform each time. The extracts are dried over potassium carbonate and concentrated, and the residue is distilled.
Yield: 6.2 g (72.8% of theory).
Boiling point 90–94° C./0.05 mbar.

EXAMPLE 16

9,9-Dimethyl-10-thia-1,4-diazatricyclo[6.3.0.0$^{2,6}$]undecane a) Ethyl 9,9-dimethyl-10-thia-1,4-diazatricyclo-[6.3.0.0$^{2,6}$]-undecane-4-carboxylate

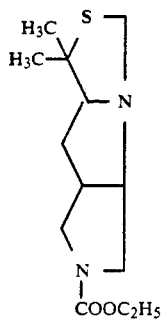

8.6 g (50 mmol) of ethyl N-allyl-N-(2-oxoethyl)-carbamate are heated under reflux overnight with 8.1 g (50 mmol) of 5,5-dimethylthiazolidine-4-carboxylic acid in 200 ml of toluene. The mixture is concentrated and the residue is distilled.

Yield: 8.4 g (62.2% of theory).

Boiling point: 141-155° C./0.03-0.05 mbar.

b) 9,9-Dimethyl-10-thia-1,4-diazatricyclo[6.3.0.0$^{2,6}$]-undecane

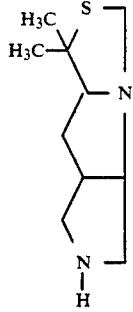

6 g (22.2 mmOl) of ethyl 9,9-dimethyl-10-thia-1,4-diazatricyclo[6.3.0.0$^{2,6}$]undecane-4-carboxylate are heated under reflux overnight with 12 g of Ba(OH)$_2$.8-H$_2$O in 100 ml of water. Potassium carbonate is added, barium carbonate is filtered off with suction and the filtrate is extracted ten times using 100 ml of chloroform each time. The extracts are dried over potassium carbonate and concentrated, and the residue is distilled.

Yield: 2.25 g (51% of theory).

Boiling point: 83° C./0.02 mbar.

EXAMPLE 17

7-Methyl-2,7-diazabicyclo[3.3.0]octane a) 2-Benzyl-7-methyl-2,7-diazabicyclo[3.3.0]octane

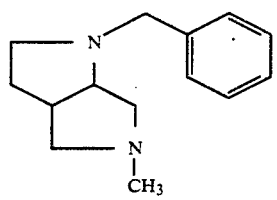

13.7 g (50 mmol) of ethyl 2-benzyldiazabicyclo-[3.3.0]octane-7-carboxylate in 20 ml of absolute tetrahydrofuran are added dropwise to 3.8 g (0.1 mol) of lithium aluminum hydride in 100 ml of absolute tetrahydrofuran. The mixture is heated under reflux overnight and decomposed successively with 4 ml each of water, 15% strength potassium hydroxide solution and water. The inorganic salts are filtered off with suction and boiled three times with 50 ml of tetrahydrofuran each time. The organic solutions are concentrated and the residue is distilled.

Yield: 10.4 g (96% of theory).

Boiling point: 90-100° C./0.1 mbar.

b) 7-Methyl-2.7-diazabicyclo[3.3.0octane

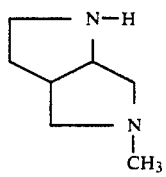

10.3 g (47.6 mmol) of 2-benzyl-7-methyl-2,7-diazabicyclo[3.3.0]octane in 200 ml of ethanol are hydrogenated at 100° C. and 100 bar on 2.5 g of palladium-active carbon (10% Pd). The catalyst is filtered off with suction, the filtrate is concentrated and the residue is distilled.

Yield: 4.2 g (69.9% of theory).

Boiling point: 50-53° C./6 mbar.

EXAMPLE 18

Benzyl-8-methyl-2,7-diazabicyclo[3.3.0]octane a) Ethyl 2-benzyl-8-methyl-2,7-diazabicyclo[3.3.0]-octane-7-carboxylate

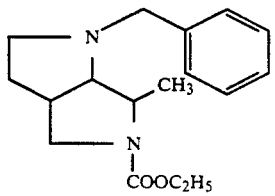

37 g (0.2 mol) of ethyl N-allyl-N-(1-oxo-2-propyl)-carbamate are heated under reflux overnight in a water separator with 33 g (0.2 mol) of N-benzylglycine in 500 ml of toluene. The mixture is concentrated and the residue is distilled.

Yield: 48.5 g (84% of theory).
Boiling point: 140–145° C./0.2 mbar.
The product is a homogeneous stereoisomer by gas chromatography.

b) 2-Benzyl-8-methyl-2,7-diazabicyclo[3.3.0]octane

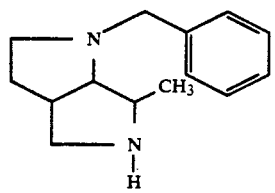

16 g (55 mmol) of ethyl 2-benzyl-8-methyl-2,7-diazabicyclo[3.3.0]octane-7-carboxylate are heated under reflux overnight with 50 ml of concentrated hydrochloric acid. The mixture is concentrated, and the residue is dissolved in 50 ml of water and rendered alkaline with potassium carbonate. The mixture is extracted five times using 50 ml of chloroform each time, the extracts are dried over $K_2CO_3$ and concentrated, and the residue is distilled.
Yield: 7.9 g (66.4% of theory).
Boiling point: 108–113° C./0.17 mbar.

EXAMPLE 19

8-Methyl-2,7-diazabicyclo[3.3.0]octane

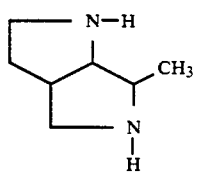

7.8 g (36 mmol) of 2-benzyl-8-methyl-2,7-diazabicyclo[3.3.0]octane in 200 ml of ethanol are hydrogenated at 100° C. and 100 bar on 2 g of palladium-active carbon (10% Pd). The catalyst is filtered off with suction, the filtrate is concentrated and the residue is distilled. The distillate crystallizes.
Yield: 3.3 g (72.7% of theory).
Boiling point: 110° C./30 mbar.
Melting point: 72–75° C.

EXAMPLE 20

Ethyl 8-methyl-2,7-diazabicyclo[3.3.0]octane-7-carboxylate

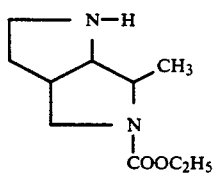

16 g (55 mmol) of ethyl 2-benzyl-8-methyl-2,7-diazabicyclo[3.3.0]octane-7-carboxylate in 300 ml of ethanol are hydrogenated at 100° C. and 100 bar on 3 g of palladium-active carbon (10% Pd). The catalyst is filtered off with suction, the filtrate is concentrated and the residue is distilled.
Yield: 9.7 g (89% of theory).

Boiling point: 100° C./0.1 mbar.

EXAMPLE 21

7,8-Dimethyl-2,7-diazabicyclo[3.3.0]octane a) 2-Benzyl-7,8-dimethyl-2,7-diazabicyclo[3.3.0]octane

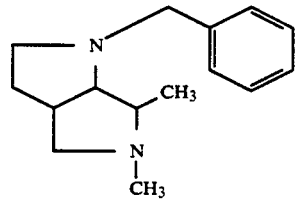

14.4 g (50 mmol) of ethyl 2-benzyl-8-methyl-2,7-diazabicyclo[3.3.0]octane-7-carboxylate in 20 ml of absolute tetrahydrofuran are added dropwise to 3.8 g (0.1 mol) of lithium aluminum hydride in 100 ml of absolute tetrahydrofuran and the mixture is then heated under reflux overnight. It is decomposed successively using 4 ml each of water, 15% strength potassium hydroxide solution and water, and the inorganic salts are filtered off with suction and boiled three times with 50 ml of tetrahydrofuran each time. The organic solutions are concentrated and the residue is distilled.
Yield: 10.9 g (94.6% of theory).
Boiling point: 105° C./0.08 mbar.

b) 7,8-Dimethyl-2,7-diazabicyclo[3.3.0]octane

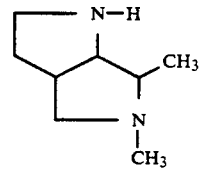

10.8 g (46.9 mmol) of 2-benzyl-7,8-dimethyl-2,7-diazabicyclo[3.3.0]octane in 200 ml of ethanol are hydrogenated at 100° C. and 100 bar on 2.5 g of palladium-active carbon. The catalyst is filtered off with suction, the filtrate is concentrated and the residue is distilled.
Yield: 4.3 g (65.4% of theory).
Boiling point: 60–62° C./6 mbar.

EXAMPLE 22

4-Methyl-2,7-diazabicyclo[3.3.0]octane a) N-(2-Buten-1-yl)-N-(2,2-dimethoxyethyl)-amine

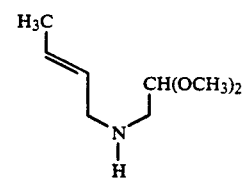

200 g of molecular sieve are initially introduced into 1,000 ml of ethanol and 105 g (1 mol) of aminoacetaldehyde dimethyl acetal and 70 g (1 mol) of crotonaldehyde are added. The mixture is allowed to stand at room temperature overnight, decanted off from molecular sieve and cooled to 0° C., and 40 g of sodium borohydride are added in 1 g portions. The mixture is then stirred overnight at room temperature and concentrated, the residue is taken up in 500 ml of water and potassium carbonate is added until an organic phase separates. This is extracted using chloroform, dried over potassium carbonate and concentrated, and the residue is distilled.

Yield: 69.5 g (41.5% of theory).
Boiling point: 85° C./12 mbar.

b) Ethyl N-(2-buten-1-yl)-N-(2,2-dimethoxyethyl) -carbamate

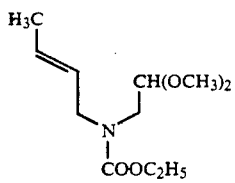

69 g (0.41 mol) of N-(2-buten-1-yl)-N-(2,2-dimethoxyethyl)-amine are dissolved in 200 ml of toluene, 30 ml of 45% strength sodium hydroxide solution are added and 43 g (0.44 mol) of ethyl chloroformate are added dropwise with ice-cooling. The mixture is stirred for a further three hours at room temperature, and the aqueous phase is separated off and extracted with 100 ml of toluene. The extract is dried over potassium carbonate and concentrated, and the residue is distilled.

Yield: 92 g (94% of theory).
Boiling point: 72° C./0.08 mbar.

Alternatively 90 g (0.5 mol) of ethyl N-(2,2-dimethoxyethyl) -carbamate are dissolved in 500 ml of toluene, 100 g of powdered potassium hydroxide and 1.5 g of triethylbenzylammonium chloride are added and 80 g (0.6 mol) of crotyl bromide (isomer mixture) are added dropwise. The mixture is stirred overnight at room temperature, the salts are dissolved in water, and the aqueous phase is separated off and extracted once using 100 ml of toluene. The extract is dried over potassium carbonate and concentrated, and the residue is distilled.

Yield: 112 g (96.8% of theory).
Boiling point: 65° C./0.1 mbar.

c) Ethyl N-(2-buten-1-yl)-N-(2-oxoethyl)-carbamate

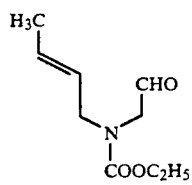

111 g (0.48 mol) of ethyl N-(2-buten-1-yl)-N -(2,2-dimethoxyethyl)-carbamate are heated under reflux for three hours with 50 g of formic acid in 950 ml of water. The mixture is saturated with sodium chloride and extracted three times using 200 ml of methylene chloride each time. The organic phases are washed with sodium hydrogen carbonate solution until neutral, dried over magnesium sulphate and concentrated, and the residue is distilled.

Yield: 77 g (86.6% of theory).
Boiling point: 94 to 100° C./0.15 mbar.

d) Ethyl 2-benzyl-4-methyl-2,7-diazabicyclo[3.3.0]-octane-7-carboxylate

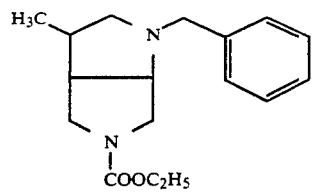

18.5 g (0.1 mol) of ethyl N-(2-buten-1-yl)-N-(2-oxoethyl)-carbamate are heated under reflux overnight in a water separator with 16.5 g (0.1 mol) of N-benzylglycine in 300 ml of toluene. The mixture is concentrated and the residue is distilled.

Yield: 10 g (25% of theory).
Boiling point: 135 to 142° C./0.1 mbar.
The product is 76% pure by gas chromatography.

e) 2-Benzyl-4-methyl-2,7-diazabicyclo[3.3.0]octane

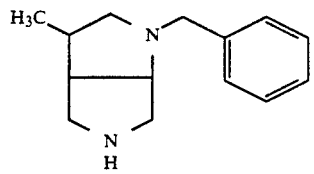

10 g (26.3 mmol) of ethyl 2-benzyl-4-methyl-2,7-diazabicyclo[[3.3.0]]octane-7-carboxylate are heated under reflux overnight with 100 ml of concentrated hydrochloric acid. The mixture is concentrated, the residue is taken up in 20 ml of water, the mixture is rendered alkaline with potassium carbonate and extracted five times using 50 ml of chloroform each time, the extracts are dried over potassium carbonate and concentrated, and the residue is distilled.

Yield: 4.6 g (81% of theory).
Boiling point: 87 to 95° C./0.13 mbar.
The product is 76% pure by gas chromatography.

f) 4-Methyl-2,7-diazabicyclo[3.3.0]octane

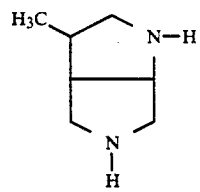

4.1 g (19 mmol) of 2-benzyl-4-methyl-2,7-diazabicyclo[3.3.0]octane in 80 ml of methanol are hydrogenated at 100° C. and 100 bar on 1 g of palladium-active carbon (10% Pd). The catalyst is filtered off with suction, the filtrate is concentrated and the residue is distilled.

Yield: 1.2 g (50% of theory).
Boiling point: 76° C./8 mbar.

EXAMPLE 23

5-Fluoromethyl-2-methyl-2,7-diazabicyclo[3.3.0]octane a) Ethyl N-(2-fluoromethylallyl)-N-(2,2-dimethoxyethyl)-carbamate

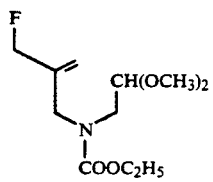

8 g (0.26 mol) of sodium hydride (80% pure) are initially introduced into 200 ml of toluene and 35.8 g (0.2 mol) of ethyl N-(2,2-dimethoxyethyl)-carbamate are added dropwise at 90° C. The mixture is then stirred for one hour at 90° C. and 32.6 g (0.3 mol) of 1-chloro-2-fluoromethylprop-2-ene are then added dropwise. The mixture is stirred overnight at 90° C., salts are dissolved in water, and the aqueous phase is separated off and extracted with toluene. The organic phases are dried over potassium carbonate and concentrated, and the residue is distilled.

Yield: 28.2 g (56.6% of theory).
Boiling point: 71 to 79° C./0.07 mbar.

b) Ethyl N-(2-fluoromethylallyl)-N-(2-oxoethyl)-carbamate

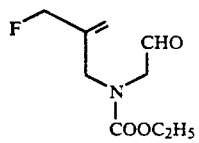

25 g (0.1 mol) of ethyl N-(2-fluoromethylallyl)-N-(2,2-dimethoxyethyl)carbamate are heated under reflux for two hours with 5 g of formic acid in 100 ml of water. The mixture is saturated with sodium chloride and extracted with methylene chloride, and the organic phases are washed with sodium hydrogen carbonate solution until neutral. They are dried over magnesium sulphate and concentrated, and the residue is distilled.

Yield: 18.5 g (87% of theory).
Boiling point: 84° C./0.18 mbar.

c) Ethyl 5-fluoromethyl-2-methyl-2,7-diazabicyclo-[3.3.0]octane-7-carboxylate

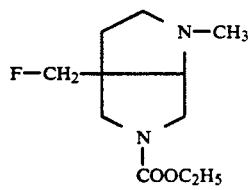

9.1 g (43 mmol) of ethyl N-(2-fluoromethylallyl)-N-(2-oxoethyl)-carbamate are heated under reflux overnight in a water separator with 3.9 g (43 mmol) of powdered sarcosine in 170 ml of toluene. The mixture is concentrated and the residue is distilled.

Yield: 7.5 g (75.8% of theory).

Boiling point: 80 to 100° C./0.25 to 0.35 mbar.

d) 5-Fluoromethyl-2-methyl-2,7-diazabicyclo[3.3.0]-octane

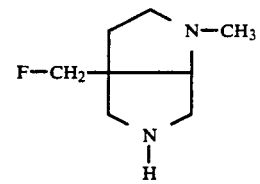

7.1 g (26 mmol) of ethyl 5-fluoromethyl-2-methyl-2,7-diazabicyclo[3.3.0]octane-7-carboxylate are heated under reflux overnight in 100 ml of concentrated hydrochloric acid. The mixture is concentrated, the residue is taken up in 20 ml of water, the mixture is rendered alkaline with potassium carbonate and extracted ten times using 50 ml of chloroform each time, the extracts are dried over potassium carbonate and concentrated, and the residue is distilled.

Yield: 0.8 g (20% of theory).
Boiling point: 34° C./0.07 mbar.

EXAMPLE 24

5-Fluoro-7-methyl-2,7-diazabicyclo[3.3.0]octane a) Ethyl N-(2,2-dimethoxyethyl)-N-(2-fluoroallyl)-carbamate

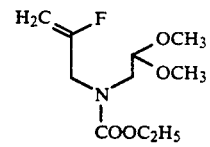

11.6 g (65.5 mmol) of ethyl N-(2,2-dimethoxyethyl)-carbamate, 15 g of powdered potassium hydroxide and 0.25 g of triethylbenzylammonium chloride are initially introduced into 65 ml of toluene and 10 g (72 mmol) of 2-fluoroallyl bromide are added dropwise at room temperature. The mixture is stirred overnight at room temperature, 100 ml of water are added, and the aqueous phase is separated off and extracted using 30 ml of toluene. The organic solutions are dried over magnesium sulphate and concentrated, and the residue is distilled.

Yield: 14.1 g (91.5% of theory).
Boiling point: 72.C/0.3 mbar.

b) Ethyl N-(2-fluoroallyl)-N-(2-oxoethyl)-carbamate

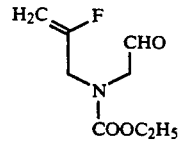

14.1 g (60 mmol) of ethyl N-(2,2-dimethoxyethyl)-N-(2-fluoroallyl)-carbamate are heated under reflux for three hours with 6.3 ml of formic acid in 120 ml of water. The solution is saturated with sodium chloride and extracted several with methylene chloride, the organic solutions are washed with saturated sodium hydrogen carbonate solution, dried over magnesium sulphate and concentrated, and the residue is distilled.

Yield: 9.8 g (86% of theory).
Boiling point: 80° C./0.25 mbar.

c) Ethyl 2-benzyl-5-fluoro-2,7-diazabicyclo[3.3.0]-octane-7-carboxylate

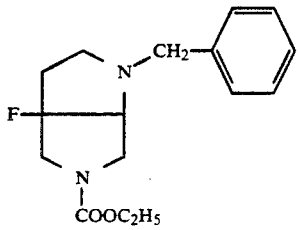

20.8 g (0.11 mol) of ethyl N-(2-fluoroallyl)-N -(2-oxoethyl)-carbamate are heated under reflux with 19 g (0.115 mol) of N-benzylglycine in 300 ml of toluene until evolution of $CO_2$ is complete. The mixture is concentrated and the residue is distilled.
Yield: 16.4 g (44.8% of theory).
Boiling point: 148-152 C/0.1 mbar.
The product is 88% pure by gas chromatography.

d) 2-Benzyl5-fluoro-7-methyl-2,7-diazabicyclo[3.3.0]-octane

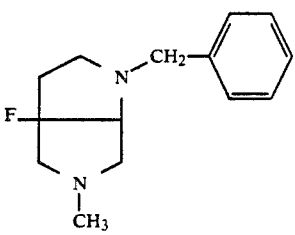

A solution of 16.4 g (49.4 mmol, 88% pure) of ethyl 2-benzyl-5-fluoro-2,7-diazabicyclo[3.3.0]octane-7-carboxylate in 25 ml of absolute tetrahydrofuran is added dropwise to 4.3 g (0.11 mol) of lithium aluminum hydride in 125 ml of absolute tetrahydrofuran and the mixture is then heated overnight under reflux. It is decomposed successively with 4.5 ml each of water, 15% strength potassium hydroxide solution and water, and the inorganic salts are filtered off with suction and boiled three times with 50 ml of tetrahdrofuran each time. The organic solutions are concentrated and the residue is distilled.
Yield: 11 g (88% of theory).
Boiling point: 98-108° C./0.08 bar.
The product is 93% pure by gas chromatography.

e) 5-Fluoro-7-methyl-2,7-diazabicyclo[3.3.0]octane

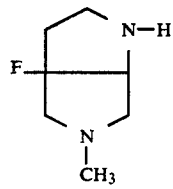

11 g (43.7 mmol, 93% pure) of 2-benzyl-5-fluoro 7-methyl-2,7-diazabicyclo[3.3.0]octane in 100 ml of ethanol are hydrogenated at 100° C. and 100 bar on 2 g of palladium-active carbon (10% Pd). The catalyst is filtered off with suction, the filtrate is concentrated and the residue is distilled.
Yield: 4.4 g (69.8% of theory).
Boiling point: 85-90° C./25 mbar.

EXAMPLE 25

Ethyl 6-methyl-2,7-diazabicyclo[3.3.0]octane-7-carboxylate a) Ethyl N-(1-buten-3-yl)-N-(2,2-dimethoxyethyl)-carbamate

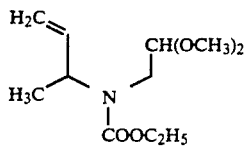

22 g (0.24 mol) of 3-chloro-1-butene are added to 35.5 g (0.2 mol) of ethyl N-(2,2-dimethoxyethyl)-carbamate and 26 g of powdered potassium hydroxide in 400 ml of dimethylformamide and the mixture is warmed overnight. to 40° C. The salts are dissolved with water and the mixture is extracted several times with methylene chloride. The organic extracts are dried over potassium carbonate and concentrated, and the residue is distilled.
Yield: 28.5 g (61.6% of theory).
Boiling point: 60 C/0.08 mbar.

b) Ethyl N-(1-buten-3-yl)-N-(2-oxoethyl)-carbamate

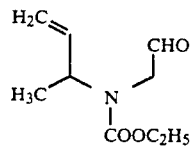

28.3 g (0.122 mol) of ethyl N-(1-buten-3-yl)-N -2,2-dimethoxyethyl)-carbamate are heated at 100° C. for one hour with 65 ml of formic acid. The mixture is poured onto 200 g of ice and extracted using methylene chloride, the organic extracts are washed with saturated sodium hydrogen carbonate solution, dried over magnesium sulphate and concentrated, and the residue is distilled.
Yield: 11.6 g (51.3% of theory).
Boiling point: 62-65° C./0.03 mbar.

c) Ethyl 2-benzyl-6-methyl-2,7-diazabicyclo[3.3.0]-octane-7-carboxylate

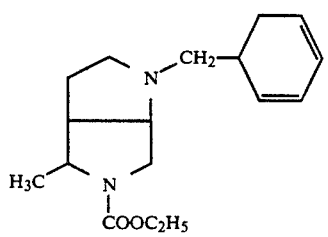

11.6 g (62.6 mmol) of ethyl N-(1-buten-3-yl)-N -(2-oxoethyl)-carbamate and 10.4 g (62.6 mmol) of N -benzylglycine in 170 ml of toluene are heated under reflux overnight in a water separator. The mixture is concentrated and the residue is distilled.
Yield: 13.7 g (75.9% of theory).
Boiling point: 140-153° C./0.1 mbar.

d) Ethyl 6-methyl-2,7-diazabicyclo[3.3.0]octane-7-carboxylate

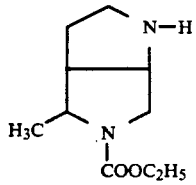

13 g (44.9 mmol) of ethyl 2-benzyl-6-methyl-2,7-diazabicyclo[3.3.0]octane-7-carboxylate in 150 ml of ethanol are hydrogenated ar 100° C. and 100 bar on 2 g of palladium-active carbon (10% Pd). The catalyst is filtered off, the filtrate is concentrated and the residue is distilled.
Yield: 6.8 g (76.4% of theory).
Boiling point: 81° C./0.09 mbar.

EXAMPLE 26

Diethyl 2,7-diazabicyclo[3.3.0]octane-3,7-dicarboxylate a) Diethyl 2-benzyl-2,7-diazabicyclo[3.3.0]octane-3,7-dicarboxylate

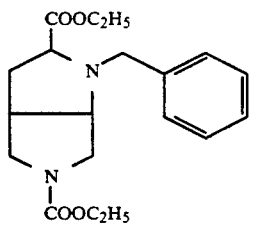

50 g (0.25 mol) of N-benzylglycine ethyl ester in 1 1 of toluene are heated under reflux in a water separator and 43 g (0.25 mol) of ethyl N-allyl-N-(2-oxoethyl)-carbamate are added dropwise during the course of two hours. The mixture is heated under reflux until water no longer separates and concentrated, and the residue is distilled.
Yield: 82.1 g (94.8% of theory).
Boiling point: 160-165° C./0.05 mbar.

b) Diethyl 2,7-diazabicyclo[3.3.0]octane-3,7-dicarboxylate

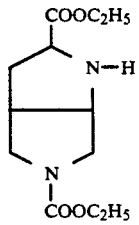

96.5 g (0.279 mol) of diethyl 2-benzyl-2,7-diazabicyclo[3.3.0]octane-3,7-dicarboxylate in 1 1 of ethanol are hydrogenated at 100 C and 100 bar on 5 g of palladium-active carbon (10% Pd). The catalyst is filtered off with suction, the filtrate is concentrated and the residue is distilled.
Yield: 63.3 g (84.6% of theory).
Boiling point: 137-140 C/0.18-0.2 mbar.

EXAMPLE 27 (FINAL PRODUCT)

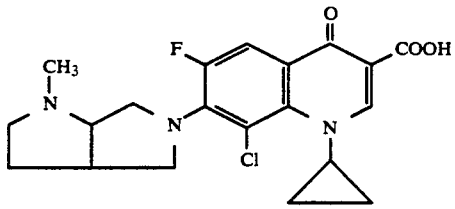

1.7 g (15 mmol) of 1,4-diazabicyclo[2.2.2]octane and 1.4 g (11 mmol) of 2-methyl-2,7-diazabicyclo[3.3.0]-octane are added to 3 g (10 mmol) of 8-chloro-1-cyclopropyl-6,7-difluoro-1,4-dihydro-4-oxo-3-quinolinecarboxylic acid in a mixture of 30 ml of acetonitrile and 15 ml of dimethylformamide and the mixture is heated under reflux for 1 hour. The mixture is evaporated, the residue is stirred with water and the undissolved precipitate is filtered off with suction, washed with water and dried at 120° C. in vacuo.
Yield: 2.4 g (59% of theory). of 8-chloro-1-cyclopropyl -6-fluoro-1,4-dihydro-7-(2-methyl-2,7-diazabicyclo[3.3.0]-oct-7-yl)-4-oxo-3-quinolinecarboxylic acid, melting point: 208-213° C. (with decomposition) (from glycol monomethyl ether).

It is understood that the specification and examples are illustrative but not limitative of the present invention and that other embodiments within the spirit and scope of the invention will suggest themselves to those skilled in the art.

We claim:

1. A 2,7-diazabicyclo [3.3.0]octane of the formula

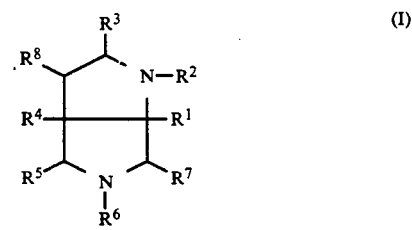

in which
$R^1$, $R^3$, $R^4$, $R^5$, $R^7$ and $R^8$ may be identical or different and in each case denote H, $C_1$-$C_5$-alkyl (optionally substituted by halogen, hydroxyl or $C_1$-$C_3$-alkoxy), $C_1$-$C_3$-alkoxycarbonyl or $C_6$-$C_{12}$-aryl,
$R^4$ additionally denotes halogen,
$R^2$ and $R^6$ may be identical or different, denote H, $C_1$-$C_6$-alkyl, benzyl, $C_6$-$C_{12}$-aryl, $C_1$-$C_3$-alkanoyl, benzoyl or $C_1$-$C_5$-alkoxycarbonyl,
excluding 2,7-diazabicyclo[3.3.0]octane.

2. A compound according to claim 1, in which
$R^1$, $R^3$, $R^4$, $R^5$, $R^7$ and $R^8$ may be identical or different and denote H, $C_1$-$C_3$-alkyl, $C_1$-$C_3$-alkoxycarbonyl or phenyl,
$R^4$ additionally denotes fluorine, chlorine or bromine,
$R^2$ and $R^6$ may be identical or different and denote H, $C_1$-$C_3$-alkyl, benzyl, $C_6$-$C_{12}$-aryl, $C_1$-$C_2$-alkanoyl, benzoyl or $C_1$-$C_4$-alkoxycarbonyl,
excluding 2,7-diazabicyclo[3.3.0]octane.

3. A compound according to claim 1, in which $R^1, R^3, R^4, R^5, R^7$ and $R^8$ may be identical or different and denote H or methyl, $R^4$ additionally denotes chlorine and bromine, $R^2$ and $R^6$ may be identical or different and denote H, methyl, phenyl, acetyl or $C_2$-$C_4$-alkoxycarbonyl, excluding 2,7-diazabicyclo[3.3.0]octane.

4. A compound according to claim 1, wherein such compound is ethyl 2,7-diazabicyclo[3.3.0]octane-2-carboxylate of the formula

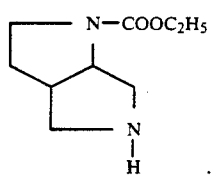

5. A compound according to claim 1, wherein such compound is 2-methyl-2,7-diazabicyclo[3.3.0]octane of the formula

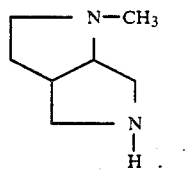

6. A compound according to claim 1, wherein such compound is 3-methyl-2,7-diazabicyclo[3.3.0]octane of the formula

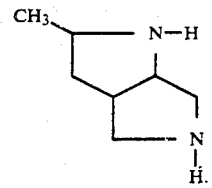

7. A compound according to claim 1, wherein such compound is 7-methyl-2,7-diazabicyclo[3.3.0]octane of the formula

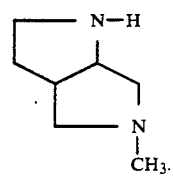

8. A compound according to claim 1, wherein such compound is 8-methyl-2,7-diazabicyclo[3.3.0]octane of the formula

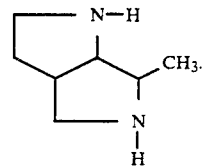

9. A compound according to claim 1, wherein such compound is diethyl 2,7-diazabicyclo[3.3.0]octane-3,7-dicarboxylate of the formula

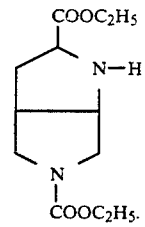

* * * * *